United States Patent [19]

Benoit

[11] Patent Number: 4,480,313
[45] Date of Patent: Oct. 30, 1984

[54] METHOD OF DETERMINING SOUND PROPAGATION

[75] Inventor: Eric Benoit, Bern, Switzerland

[73] Assignee: Polytronic AG, Muri, Switzerland

[21] Appl. No.: 334,469

[22] Filed: Dec. 28, 1981

[30] Foreign Application Priority Data

Dec. 30, 1980 [CH] Switzerland ............... 9629/80

[51] Int. Cl.³ .................................. G01P 5/00
[52] U.S. Cl. ...................................... 364/565; 73/579
[58] Field of Search ............... 364/410, 509, 510, 517,
364/565; 367/13, 902, 906; 73/24, 579, 597,
861.28; 324/160; 181/160, 196

[56] References Cited

U.S. PATENT DOCUMENTS 2,758,663  8/1956  Snavely .................... 73/597
3,009,104  11/1961 Brown ...................... 73/597
3,697,936  10/1972 Zacharias, Jr. et al. ...... 73/597
4,303,853  12/1981 Thalmann .................. 367/906

Primary Examiner—Edward J. Wise
Assistant Examiner—Edward R. Cosimano
Attorney, Agent, or Firm—Karl F. Ross; Herbert Dubno

[57] ABSTRACT

A method of and an apparatus for determining sound propagation speed in a medium which is subject to variations in this speed. A measuring tube containing the medium is energized by a loudspeaker (ultraacoustic transducers) with a controllable energizing frequency in resonance with the measuring tube containing a column of the medium to be evaluated. The resonant output frequency is detected and modulated with a low frequency signal and the mean value of the modulated output signal is formed and counted. For a predetermined count, the elapsed time is measured and from this value the propagation velocity is calculated.

4 Claims, 4 Drawing Figures

METHOD OF DETERMINING SOUND PROPAGATION

FIELD OF THE INVENTION

My present invention relates to a method of determining the sound propagation speed or velocity in a medium in which the speed may vary and, more particularly, to the determination of sound propagation velocity in a fluid such as air in which the sound propagation velocity is inter alia a function of the temperature.

BACKGROUND OF THE INVENTION

In various industrial, technological and scientific fields, it is frequently necessary to determine instantaneous values of sound propagation speed or velocity. For example, many systems depend upon the sound propagation velocity in air which varies nonlinearly as a function of the temperature and, to date, instantaneous values of the sound propagation velocity in air could not be obtained in a simple and convenient manner or with relatively simple apparatuses. Indeed, repeated or continuous monitoring of the sound propagation velocity in air subject to temperature fluctuations has not been possible.

To measure sound propagation velocity, it is known to provide a glass tube filled with air which has a closure at an end of the air-filled column, which is subject to movement and to which a predetermined acoustical frequency (a harmonic of the fundamental) can be applied so that the mechanical displacement results in a resonance wave within the tube. The resonance is established by changing the effective length of the column by movement of this member and the longitudinal wave established in the air column can be made visible by the use of cork dust or powder which develops nodes or condensation patterns separated by rarefaction patterns.

The wavelength can be measured from the cork powder patterns and the sound propagation velocity calculated.

In German patent document DE-OS No. 29 43 766 and the corresponding U.S. Pat. No. 4,303,853, issued Dec. 1, 1981, commonly assigned with the present case, a method of and an apparatus for determining the impact site of a bullet upon a target has been described. In principle, this system utilizes the time-staggered pick-up of acoustic signals by a plurality of spaced-apart acoustoelectrical transducers to provide an indication of the location of the point of impact upon the target.

The location, of course, can only be determined with precision if the sound propagation velocity of the medium between the target surface and these transducers is known with equal or greater precision.

In closed target assemblies of the aforedescribed type, it has been shown experimentally that the temperature is not constant but continuously varies and that the sound propagation velocity is a nonlinear response to this continuously fluctuating temperature. Because of this phenomenon, the mathematics for calculating the impact location are complex and it is not uncommon, unless significant effort is made to minimize the temperature change, for the precision of the measurement to lie below the minimum standards of the UIT (Union Internationale de Tir).

Since methods and devices for measuring the said propagation velocity, which would have enabled the system of the aforementioned patent to be utilized with precision, were not then available, that patent describes means for minimizing temperature fluctuations and thereby maintaining the sound propagation velocity practically constant.

For such apparatus and other applications in the field of technology, industry and research, it is important to have means for determining instantaneous values of sound propagation velocity.

OBJECTS OF THE INVENTION

It is the principal object of this invention to provide an improved method of determining sound propagation velocity in a medium in which this velocity is prone to change.

Yet another object of this invention is to provide an improved target system which eliminates the need for carefully controlling the temperature within the space between the target surface and the acoustic sensors.

Yet a further object of this invention is to provide a method of determining the sound propagation velocity in a changeable medium such as air.

SUMMARY OF THE INVENTION

These objects and others which will become apparent hereinafter are obtained, in accordance with the present invention, with a system which comprises the use of a measuring tube forming a column of a medium in which the sound propagation velocity is to be determined and which enables energization of this column with a controllable energization frequency in resonance with the tube to produce a resonant output frequency.

The resonant output frequency is detected, e.g. by an acoustic electric transducer such as a microphone, and the resulting output frequency signal is delivered to the circuit in which it is added or modulated with a lower frequency signal. The average or mean value of the output frequency is formed, e.g. as another signal, and for a predetermined number of counts of this signal between a starting signal and an ending signal, the time is determined, this time being utilized to calculate the propagation speed. Means is provided to vary the energization frequency applied to obtain the resonant output frequency.

Experiments have shown that, especially for measurement of the sound propagation velocity in association with a target, the resonant output frequency should be modulated with a frequency which is 100 times to 5000 times less. In other words, for an output frequency F, the low modulation frequency f is defined by the relation $5000f \geq F \geq 100f$. The low frequency signal also serves as the enabling or teaching signal for initiating the counting operation.

Advantageously, a number N of pulses are counted and the calculation of the sound propagation speed or velocity s is effected in accordance with the relationship $$s = N \cdot (\lambda/t)(m/s) \qquad (1)$$

wherein $\lambda$ is the wavelength and t the time elapsed between the first and the last pulses, i.e. from the triggering pulse to the final pulse or period of the predetermined number of pulses.

Naturally, this formula can be built into an automatic computing device as an algorithm so that the apparatus of the invention automatically displays the sound propagation velocity on command.

Because of the accuracy with which the measurement can be carried out in accordance with the invention, it is not necessary to determine any of the other parameters which have hitherto been associated with measurements of sound propagation speeds in media of varying density or temperature.

According to another aspect of the invention, a device or apparatus for determining the sound propagation velocity in a medium of varying density or temperature comprises a support for the column of the medium studied, namely a tube containing the column and a support in which this tube is preferably adjustably mounted in a horizontal orientation.

As will be apparent hereinafter this tube can be closed at one or both ends and is juxtaposed with means, e.g. the electro-acoustical transducer, for applying an activating acoustical signal of adjustable but predetermined frequency to the column. This electroacoustical transducer can be a loudspeaker and the pick-up for the output frequency can be a microphone or some other acousto-electric transducer.

The measurement tube, loudspeaker and sound pick-up are connected in a circuit with a frequency-voltage converter to generate an electrical output signal which corresponds to the output frequency formed in the medium column and proportional to the sound propagation velocity thereof.

The circuit also includes a modulator supplied with the low frequency signal to modulate the output frequency signal and counting means for counting a predetermined number of periods of the output frequency as well as timer means for measuring the time interval between the first and last period which are counted and generating an output representing the sound propagation velocity s based upon its proportionality to the measured time interval t in accordance with formula (1) given above.

When the system of this invention is used in conjunction with or as part of a target system for signaling the location of impact upon a target based upon acoustical transmission through air between the target surface and respective acoustic pick-up, it has been found to be advantageous to provide the measuring tube of a length which is equal to an integral number of quarter wavelengths, i.e.

$$L_1 = m\lambda/4 \qquad (2)$$

where
$L_1$ is the length of the measuring tube,
m is an integer and
$\lambda$ is the wavelength.

Furthermore the distance between the acoustical pick-up and the end of the tube turned away from the loudspeaker should be an integral number of quarter wavelengths, i.e.

$$L_2 = p\lambda/4 \qquad (3)$$

where
p is an integer less than m and
$L_2$ is the distance between the end of the measuring tube turned away from the loudspeaker to the sound pick-up or microphone.

The distance between the loudspeaker and the end of the measuring tube turned toward it also may be an integral number of quarter wavelengths so that $$L_3 = q\lambda/4 \qquad (4)$$

where
q is an integer which can be equal to or less than p and
$L_3$ is the distance between the microphone and the measuring tube.

Using the system of the invention it is not only possible to instantaneously and at will determine the sound propagation velocity in the air for use in conjunction with the target system of the aforementioned patent, but it will also be possible to measure the sound propagation speeds in other media and for other purposes. For example, it is possible to determine the mole-mass in a gas mixture, in length of a liquid column, the proportions of components of a medium of known composition and the like.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 1:
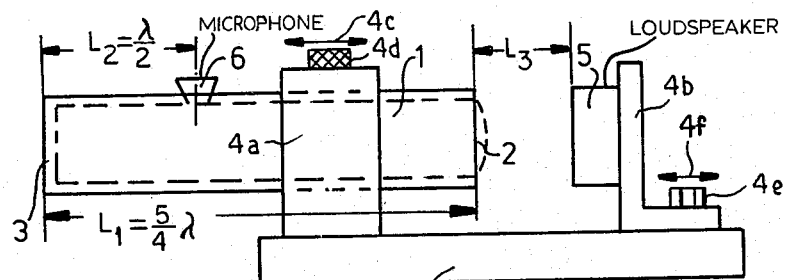
FIG. 1 is a diagrammatic side elevational view of the measuring tube, microphone and acoustic pick-up utilized in accordance with the present invention.

The unit shown in FIG. 1 is placed in whatever environment must be evaluated as to sound propagation velocity. For example, in the case of a target, this unit can be disposed in the space between the target surface and the acoustic pick-up which respond to impact against the target surfaces. Depending upon the application of the information obtained, the device may be utilized elsewhere.

The device shown in FIG. 1 comprises a support 4 provided with a bracket 4a with a bore in which a measuring tube is received.

An open end 2 of this measuring tube is turned toward but spaced from a loudspeaker 5 which is mounted, in turn, on another bracket 4b. The tube 1 can be shifted as indicated by the arrow 4c in the bracket 4a upon release of a locking screw 4d while the microphone can be moved relative to the tube upon release of a nut 4e and shifting of the bracket 4b in the direction of arrow 4f via a guideway (not shown) provided for that purpose.

The wall of tube 1 is also provided with an acoustic electric transducer or pick-up in the form of a microphone 6 shown to be set into this wall and in direct contact with the medium in the tube.

The nut 4e on movement at the bracket 4b permits adjustment of the distance $L_3$ between the loudspeaker 5 and the end tube of the tube 1 proximal to that loudspeaker, release of the screw 4d subserves a similar function. The length of the tube 1 is represented at $L_1$ and the distance $L_2$ is measured from the closed end 3 of tube 1 to the microphone 6.

It has been found that the most effective results for the target system described can be obtained when $m=5$; $p=1$ and $q=1$, i.e. when the length of the tube $L_1$ is $5/4\lambda$, the distance $L_2$ of the microphone from the closed end 3 of the tube is $\lambda/4$ and the distance between the microphone and the inlet opening of the tube 1 is $\lambda/4$. The measuring tube can be composed of iron or glass. The relative adjustability of the loudspeaker and measuring tube has been found to be important when the device is used in other applications as well.

It should be noted that depending upon the formula used to determine the sound propagation speed and hence the algorithm which is programmed into the circuit outputting the signal proportional to this speed, both ends of the measuring tube may be opened or both ends closed. These modifications only vary the characteristic frequency of the tube which otherwise remains operative for the purposes of the invention. When both ends of the tubes are closed, lateral openings are provided as an inlet and outlet for the medium, these openings being formed in the cylindrical wall of the tube.

Figure 2:
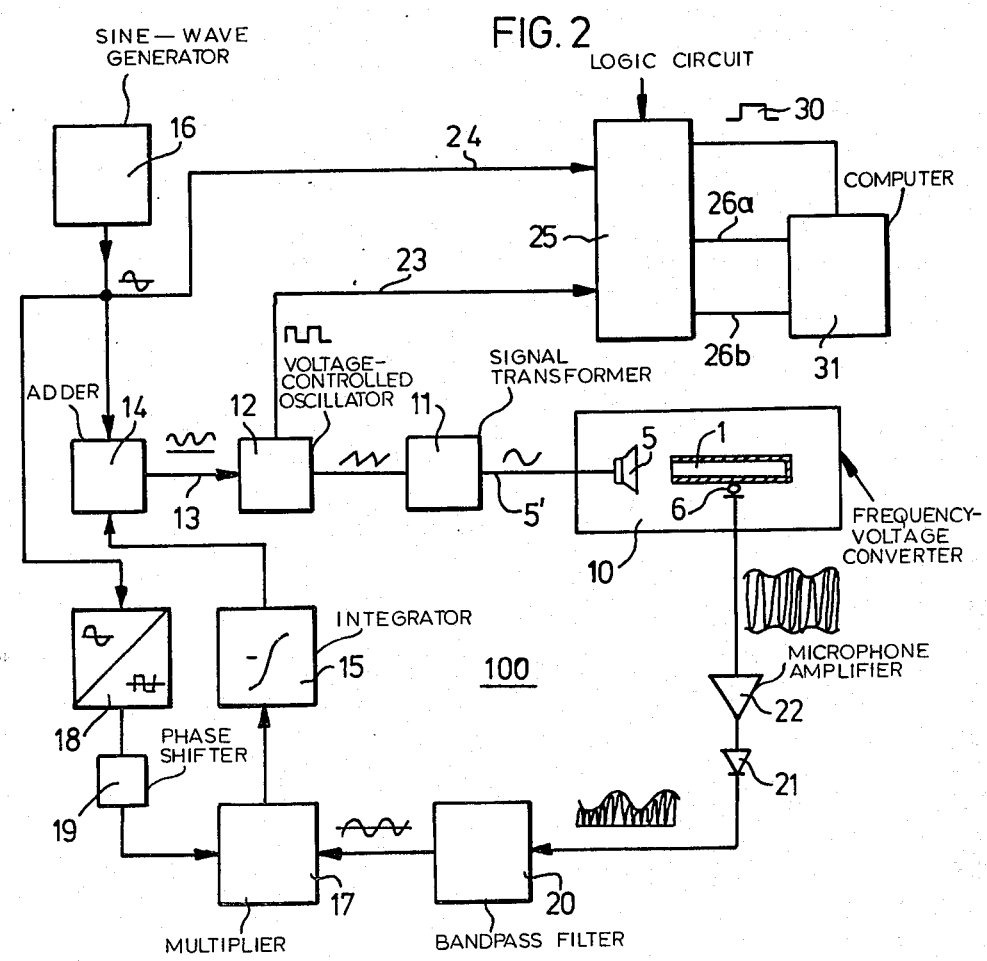
FIG. 2 is a schematic diagram in block form showing the circuitry utilized in accordance with this invention to generate output signals proportioned to the sound propagation speed as detected in the measuring tube of FIG. 1.

The assembly shown in FIG. 1 and at 10 in FIG. 2 constitutes a quasi frequency-voltage converter which is connected in a circuit 100 which serves to generate an output signal proportional to the sound propagation velocity.

As will be apparent from the following discussion, the entire system operates a frequency follower analogous to the voltage followers of operational amplifier systems (see *Operational Amplifiers*, McGraw Hill Book Company, New York, 1971, pp 430 ff.).

The loudspeaker 5 of the converter or measuring-tube assembly 10 receives a signal from the main signal generator 12 which is a voltage control oscillator whose frequency is proportional to an applied control voltage. This signal, delivered by a signal transformer 11, inverting every second pulse and smoothing the signal, can have a frequency of 2.4 to 2.9 KHz. The voltage controlled oscillator can be of the type described in *Handbook of Telemetry and Remote Control* (McGraw Hill Book Company, New York, 1967, chapter 6, pp. 22 ff.).

The input to the voltage controlled oscillator 12 is supplied by a line 13 from an adder stage 14 (pp. 338 ff. of *Pulse, Digital and Switching Waveforms*, McGraw Hill Book Company, New York, 1965) which reduce the output voltage from an integrator 15 (pp. 313 ff. of *Operational Amplifiers*) and a 4 Hz modulation signal from a 4 Hz wave generator 16. A waveform generator for this purpose is described in pages 381 to 393 of *Operational Amplifiers*.

Feedback coupling is provided by a multiplier 17 (chapter 15, pages 75 ff. of the *Handbook of Telemetry and Remote Control*) operating a synchronization detector. This multiplier 17 receives a signal from the signal transformer 18, which can be a waveform squarer and a phase shifter 19 (see page 726 of *Pulse, Digital and Switching Waveforms*). This signal has a frequency of 4 Hz. The other signal applied to the multiplier 17 is the signal derived from the microphone 6, amplified by the microphone amplifier 22 and fed to the multiplier 17 via a rectifier 21 and a bandpass filter 20. Circuits for this purpose can also be found in the reference works mentioned previously.

As will be apparent from FIG. 2, the frequency output 23 of the main oscillator 12 as well as a 4 Hz signal from the sine-wave generator 16 via line 24 are delivered to the logic circuit 25 at the output of which signals are delivered at 26a and 26b for further processing as will be described below for effecting the mathematical operations to yield the instantaneous sound propagation velocity in the measuring tube 1. The converter unit and computer 31 can also include a display for this sound propagation velocity value. While the circuitry shown in FIG. 2 is the preferred and best mode circuit in accordance with this invention, it should be noted that other circuitry can be utilized to achieve a similar end.

The integrator corrects its output voltage as long as the mean value of the voltage from the multiplier 17, which acts as a synchronizing detector, remains zero.

The operation is described below based upon physical principles which are also set forth.

The intrinsic characteristic frequency for the measuring tube 1, when the latter is opened or closed at both ends, can be given by the formula $$fn = \frac{n \cdot c}{2 \cdot l} \; ; n = 1.23. \qquad (5)$$

For the measuring tube 1 (FIG. 1) which is closed at one end, the following formula applies:

$$fn = (n - \tfrac{1}{2})\frac{c}{2 \cdot l} \; ; n = 1.23. \qquad (6)$$

In these formulae:
f equals the frequency in Hz,
n equals the order of the characteristic frequency (fundamental frequency and harmonics),
c equals sound velocity
l equals length of measuring tube in meters.

The sound velocity c in gas is given by the following relationship:

$$c = \sqrt{\frac{\gamma RT}{M}} \;\; (m/s) \qquad (7)$$

where
c equals velocity (m/s)
R equals the gas constant (Juels/KMoL°K).
T equals the absolute temperature (°K)
$\gamma$ equals the adiabatic exponent and
M equals the mole mass (Kg/KMol).

The frequency/velocity relationship is the following $$f = c/\lambda \qquad (8)$$

where
f is the frequency
c is the sound propagation velocity
$\lambda$ is the wavelength.
Preferably $\lambda$ is given by the relationship $$\lambda = 4/5l \qquad (9)$$

wherein
$\lambda$ is the wavelength and
l is the length of the measuring tube.

For determining the sound propagation velocity in the air column of the measuring tube 1, which is proportional to the mean resonance frequency, the activating frequency which is radiated to the tube via the loudspeaker 5 is automatically set to the oscillation maximum of the measuring tube 1. This control is effected in about one minute. The signal, modulated with the 4 Hz low frequency signal, thus corresponds to the output frequency which is proportional to the sound propagation velocity modulated with a frequency which is 100 to 5000 times smaller.

Figure 3:
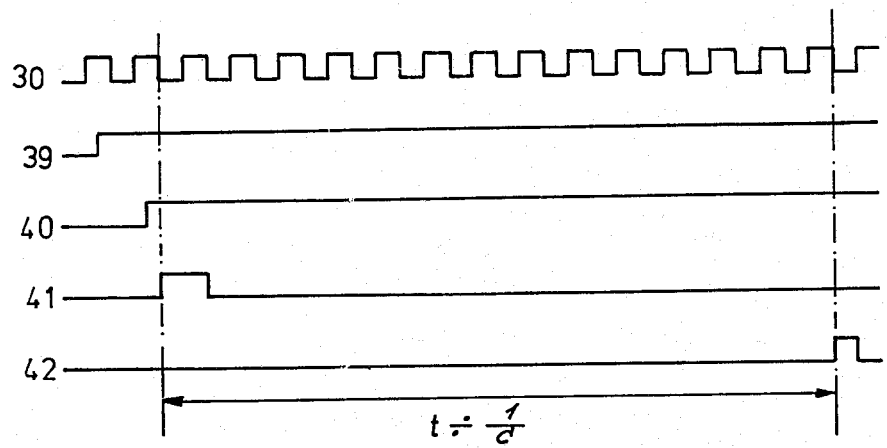
FIG. 3 is a pulse diagram in which pulse amplitude is plotted along the ordinate versus time along the abscissa illustrating principles of this invention.

The mean value of this modulated output frequency is subjected to time measurement in order to calculate the sound propagation velocity as is apparent from FIG. 3. To this end, the logic circuit 25 delivers a measurement command 39 which, at the next zero-transition of 4 Hz modulation wave (curve 40 in FIG. 3) triggers a starting pulse 41 with the next negative flank of the main or resonance frequency (2.7 Hz). After a predetermined number of periods, fourteen being preferred, a stop pulse 42 is generated. Thus the stop pulse 42 is produced as soon as 14 negative flanks of the main frequency have been counted. These pulses are delivered via the outputs 26a and 26b of the logic circuit 25 to the computer 31 which also receives clock pulses 30 and thus can determine the time t between the starting pulse and the stopping pulse for calculation of the sound velocity in accordance with the formula $$s = 14 \cdot (\lambda/t)(m/s), \quad (10)$$

where $\lambda$ is the wavelength.

As can be readily seen therefore it is possible to trigger a series of measurements as the air column in tube 1 changes, generally as a result of changes in the condition of the ambient air so that the displayed result or the computed result is a series of corrected delays of the sound propagation velocity.

Thus, it is important for the purposes of the invention that the circuit be capable of compensating the activation frequency to the changing resonance conditions of the medium-containing tube so that an output can be obtained from the latter which is always proportional to the sound propagation velocity thereby enabling the elapsed time for a predetermined number of wave lengths to provide an indication of this velocity.

Naturally, the system is capable of measuring changes in the said propagation velocity in a varying medium such as ambient air in the manner described or of measuring other useful parameters when the sound propagation velocity is held constant, for example, utilizing the relationship given above it is possible to determine the mole-mass of a gas mixture if its composition is held constant. For environmental protection purposes, one can utilize this system to determine the propagation of nitrogen in a waste gas or other compositional parameters.

Furthermore for a known and constant sound propagation velocity it is possible to utilize the relationships given previously to determine the length of a fluid column which might not otherwise be accessible. Thus, composition, physical and other measurements, including temperature measurements, may be made with ease.

As a consequence the method and apparatus of the invention has a wide spectrum of uses.

I have found, however, that this apparatus and method is especially effective for the measurement of sound propagation velocity of the ambient air in conjunction with the targeting system of the type described in the aforementioned patent utilizing electronic detection of acoustic signals. Such a targeting arrangement has been shown in FIG. 4.

Figure 4:
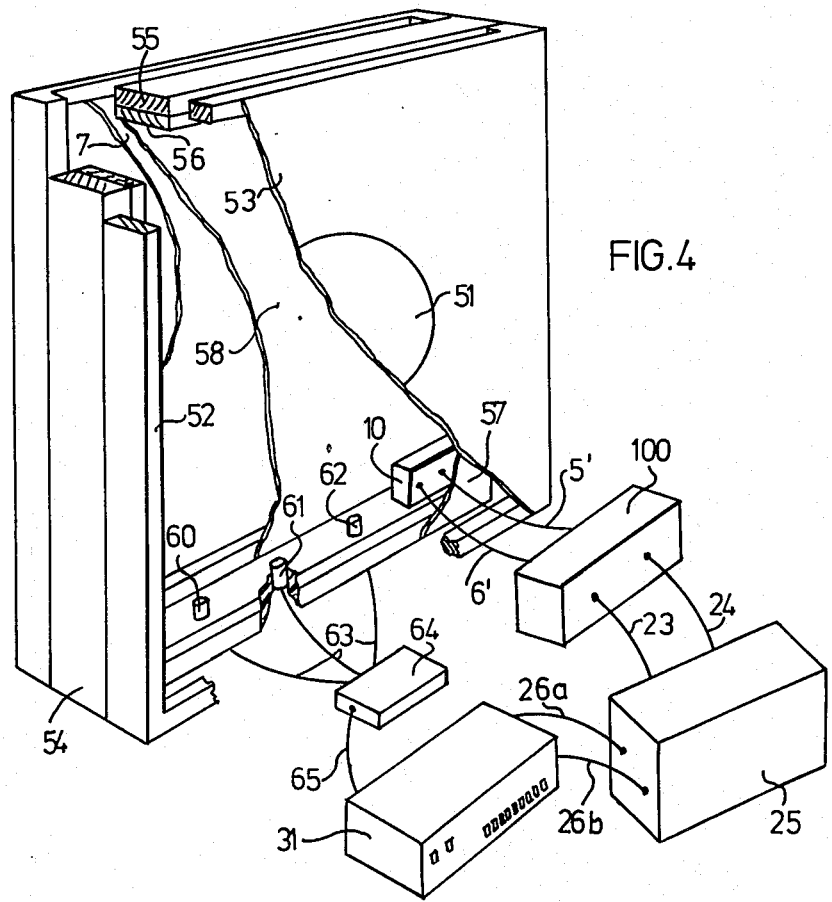
FIG. 4 is a perspective view partly broken away of a target system embodying this invention but operating in accordance with the principles described in the commonly owned U.S. Pat. No. 4,303,853.

The target of FIG. 4 comprises a target image 51 upon a sheet 53 spanning a wooden frame 52. Rearwardly of this sheet in the direction of travel of a bullet, the frame 52 is affixed to a further wooden frame 54 which defines a measuring member.

As can be seen from the section portions of FIG. 4, the measuring chamber frame 54 is lined with a thermal insulation layer 55 and is bounded by a sound-absorption layer 56.

The measuring chamber is further defined by a front sheet 57, preferably having a thickness of about 4 to 5 mm and a rear sheet 58 similar to the front sheet and, like the front sheet, forming a membrane.

These sheets generally are multilayer laminates on a synthetic resin foil carrier and can include an internal sound-absorbent layer and an external sound-reflectant layer.

Within the measuring chamber, preferably on the lower member of the frame 54, three acoustic pick-ups 60, 61 and 62 (acousto electric transducers) are provided, these pick-ups being connected at 63 with an amplifier 64 which, in turn, is connected at 65 with a calculator 31.

Within the measuring chamber, the measuring tube unit 10 previously described is also disposed and is connected via lines 5' and 6' within circuit 100 whose conductors 23 and 24 turn to the logic unit 25. The outputs 25a and 25b of the logic unit 25 extend to the computer 31, which, in this case, also can display proximity of the impact upon the target of the bullet to the center of the target pattern 51.

Thus, this system, which operates generally in the manner described in the aforementioned patent, can compensate for variation of sound propagation velocity so as to be of increased precision.

I claim:
1. A method of determining the sound propagation velocity in a medium comprising the steps of:
   (a) forming a column of said medium in a measuring tube;
   (b) activating said column with acoustic energy of a controllable activation frequency in resonance with said measuring tube;
   (c) picking up from said measuring tube a resonant output frequency and transforming same into a corresponding output frequency signal;
   (d) modulating said output frequency signal with a modulating signal of substantially lower frequency, thereby providing a composite output signal;
   (e) forming a mean value from said composite output signal; and
   (f) counting a predetermined number of periods of the mean value of the composite output signal and determining the elapsed time of the resulting count such that said elapsed time is proportional to the sound propagation velocity in said medium, said propagation velocity being determined automatically in accordance with the relationship

$$s = N \cdot (\lambda/t)(m/s) \quad (11)$$

wherein N is the number of counted periods, $\lambda$ is the wavelength and t the time between the first and last counted periods.

2. The method defined in claim 1, further comprising automatically transforming said elapsed time into a signal proportional to sound propagation velocity in said medium.

3. The method defined in claim 1, wherein said low frequency modulation signal has a frequency of 100 to 5000 times less than the resonant output frequency.

4. The method defined in claim 1 wherein said low frequency signal triggers a starting pulse to initiate the count.

* * * * *